United States Patent
Coles

[19]

[11] Patent Number: 6,132,691
[45] Date of Patent: Oct. 17, 2000

[54] STATION FOR SOAKING INTRACAVITY PROBES

[76] Inventor: Philip R. Coles, PCI Medical Inc., P.O. Box 188, Deep River, Conn. 06417

[21] Appl. No.: 09/157,261

[22] Filed: Sep. 21, 1998

[51] Int. Cl.⁷ ........................................................ A61L 2/18
[52] U.S. Cl. ............................................ 422/300; 206/210
[58] Field of Search ........................ 422/300; 206/209.1, 206/210, 207

[56] References Cited

U.S. PATENT DOCUMENTS

| | | | |
|---|---|---|---|
| 1,987,472 | 1/1935 | Feldon | 422/300 X |
| 2,012,685 | 8/1935 | La Posea . | |
| 2,457,500 | 12/1948 | Scandura . | |
| 4,473,152 | 9/1984 | Jump, Jr. et al. | 206/209.1 |
| 4,585,119 | 4/1986 | Boyington | 206/209.1 |
| 4,748,007 | 5/1988 | Gaudion et al. | 422/300 |
| 4,995,509 | 2/1991 | Kornfeind | 206/209.1 |
| 5,086,916 | 2/1992 | Gray | 422/300 X |
| 5,090,433 | 2/1992 | Kamaga | 134/169 C |
| 5,137,689 | 8/1992 | Cantrell | 422/28 |
| 5,288,467 | 2/1994 | Biermaier | 422/116 |
| 5,310,524 | 5/1994 | Campbell et al. | 422/33 |
| 5,476,107 | 12/1995 | Oakley et al. | 128/897 |

*Primary Examiner*—Elizabeth McKane
*Attorney, Agent, or Firm*—Richard L. Miller

[57] ABSTRACT

A station for soaking intracavity probes is disclosed. The station includes a housing that either rests on a generally horizontal surface or mounts to a generally vertical surface, and at least two containers that are replaceably positioned in the housing and contain a disinfectant and a rinsing agent. The housing contains a container compartment that replaceably holds the at least two containers, a filter compartment in which a carbon filter resides for filtering out the noxious and/toxic fumes passing therethrough, an electrical connector compartment for holding the electrical connectors of the intracavity probes while the intracavity probes are being soaked in the at least two containers which keeps the electrical connectors safely out of the way during soaking, and a machine compartment that contains an electric fan that moves the noxious and/or toxic fumes from the container compartment through a first partition in the housing, through a second partition in the housing, through the carbon filter, through a third partition in the housing, and out through a plurality of vent holes in at least one side wall of the housing.

16 Claims, 1 Drawing Sheet

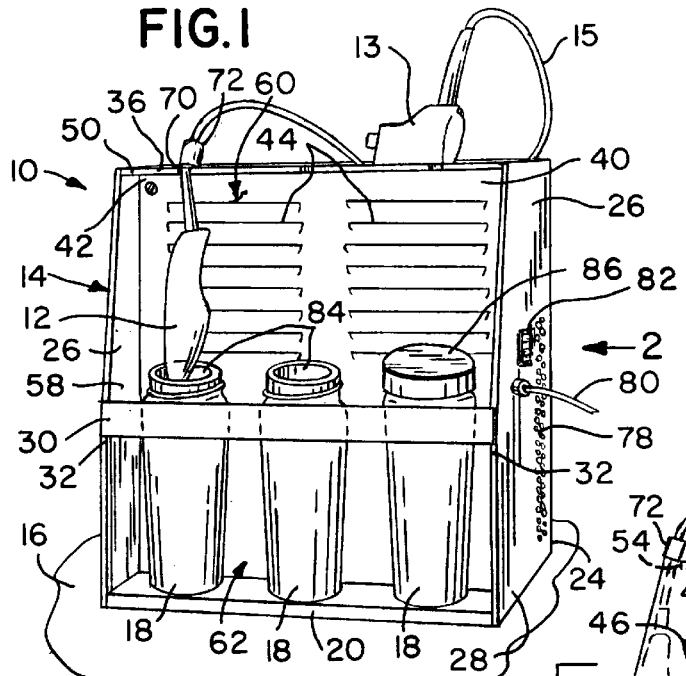
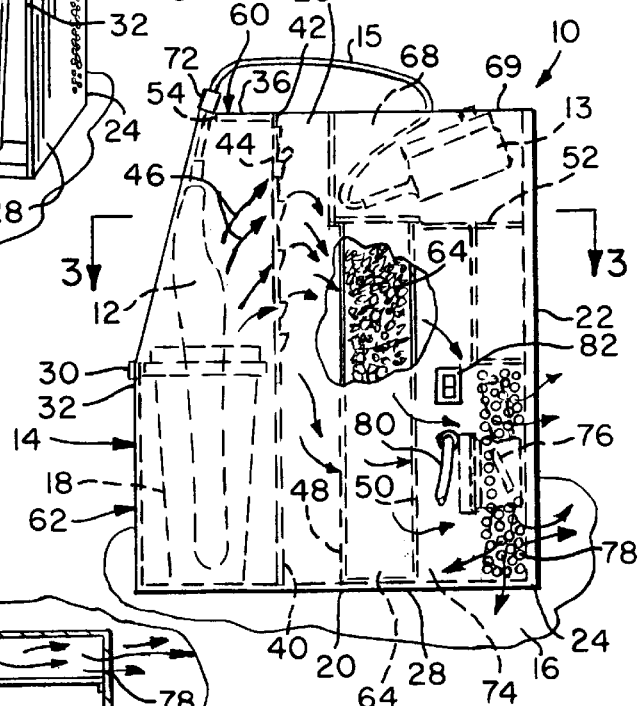
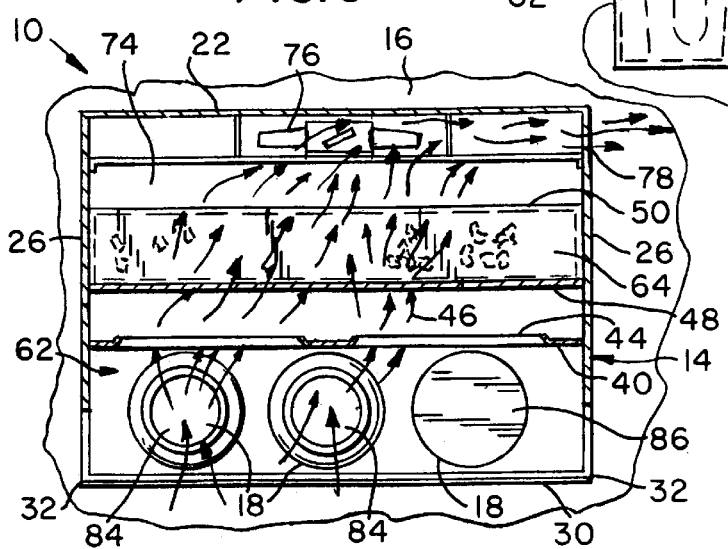

STATION FOR SOAKING INTRACAVITY PROBES

BACKGROUND OF THE INVENTION

1. Field of the Invention

The present invention relates to a soaking station. More particularly, the present invention relates to a station for soaking intracavity probes.

2. Description of the Prior Art

Numerous innovations for medical instrument cleaning devices have been provided in the prior art that will be described. Even though these innovations may be suitable for the specific individual purposes to which they address, however, they differ from the present invention.

A FIRST EXAMPLE, U.S. Pat. No. 5,090,433 to Kamaga teaches a cleaning apparatus used for cleaning a scope of an endoscope after completing medical inspection by the endoscope. The cleaning apparatus has a cylindrical cleaning vessel. This cylindrical cleaning vessel includes top and bottom portions, a scope insertion hole formed in the top portion, and a cleaning fluid conducting hole formed in the bottom portion. This cylindrical cleaning vessel is detachably mounted on a rod of a scope stand.

A SECOND EXAMPLE, U.S. Pat. No. 5,137,689 to Cantrell teaches pressurized liquid that is forced through the instrument simultaneous with submerging in a container of disinfectant or sterilization solution and also a gas may be introduced. The containers of the solutions receive the instrument which is mounted to be driven from one container to another, selectively by electric motors which are controlled through an electrical circuit that also operates pumps and valves in a pre-determined sequence of operations.

A THIRD EXAMPLE, U.S. Pat. No. 5,288,467 to Biermaier teaches a cleaning and disinfecting apparatus for medical equipment and instruments. The apparatus includes at least one feed line constructed so as to be coupled for the supply of cleansing liquid and at least one outlet line for the discharge of spent cleansing liquid. A transportation and cleaning vessel is further provided which receives the articles to be cleaned and is adapted to be placed in and taken out of the apparatus. The vessel has at least one inlet and at least one outlet, the inlet being adapted to be connected to the feed line and the outlet being adapted for coupling to the discharge line. The inlets and outlets can be closed by non-return flaps on valves which are in closed position when inoperative and are opened by pressurized fluid.

A FOURTH EXAMPLE, U.S. Pat. No. 5,310,524 to Campbell et al. teaches a system for reprocessing and sterilizing a previously used catheter having at least one lumen. The catheter is provided with a housing and enclosed within the housing. Heated sterilant is provided to the housing and the catheter. The lumen is tested during the reprocessing and sterilizing cycle for blockages and integrity. If the catheter is of a type having a balloon tip, the balloon is also tested for integrity by inflating and deflating it a plurality of times. The housing is pressurized to a level above the ambient pressure and maintained at such pressure whereby the sterility of the catheter is maintained for up to one week. Further disclosed is an apparatus for selectively coupling used catheters to a source of sterilant. The apparatus includes a housing having a tray for holding the catheter in place during reprocessing, a door for enclosing and locking the catheter within the housing, and a plurality of valves for coupling the housing to a source of sterilant. In addition, the apparatus includes a cap for maintaining the sterility of the catheter during storage.

A FIFTH EXAMPLE, U.S. Pat. No. 5,476,107 to Oakley et al. teaches apparatus for disinfecting electronic probes used in surgical procedures that comprises a housing for containing a disinfecting fluid and including a dummy connector for forming a sealed connection to the cable, connector by which the probe is connected to associated equipment, whereby the contacts of the cable connector are protected from exposure to the disinfecting fluid.

It is apparent that numerous innovations for medical instrument cleaning devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

The present invention meets OSHA and JCAHO requirements for the safe use of glutaraldehyde and other chemicals, eliminates fumes, no duck work needed, and can be wall mounted or placed on a counter.

The present invention treats 60 CFM of air, at an average face velocity (FPM) of 80, uses 110V, 60 hz, and 20 watts, weighs 25 lbs., and its disinfection containers are 1 quart each.

ACCORDINGLY, AN OBJECT of the present invention is to provide a station for soaking intracavity probes that avoids the disadvantages of the prior art.

ANOTHER OBJECT of the present invention is to provide a station for soaking intracavity probes that is simple and inexpensive to manufacture.

STILL ANOTHER OBJECT of the present invention is to provide a station for soaking intracavity probes that is simple to use.

BRIEFLY STATED, YET ANOTHER OBJECT of the present invention is to provide a station for soaking intracavity probes. The station includes a housing that either rests on a generally horizontal surface or mounts to a generally vertical surface, and at least two containers that are replaceably positioned in the housing and contain a disinfectant and a rinsing agent. The housing contains a container compartment that replaceably holds the at least two containers, a filter compartment in which a carbon filter resides for filtering out the noxious and/toxic fumes passing therethrough, an electrical connector compartment for holding the electrical connectors of the intracavity probes while the intracavity probes are being soaked in the at least two containers which keeps the electrical connectors safely out of the way during soaking, and a machine compartment that contains an electric fan that moves the noxious and/or toxic fumes from the container compartment through a first partition in the housing, through a second partition in the housing, through the carbon filter, through a third partition in the housing, and out through a plurality of vent holes in at least one side wall of the housing. The electrical cords are draped over a top cross member of the housing and pass through notches in the top cross member. The intracavity probes are suspended in the at least two containers which prevents costly damage to their sensitive tips, by adjustable holder clips that clip onto the electrical cords, and which rest on the top cross member.

The novel features which are considered characteristic of the present invention are set forth in the appended claims.

The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows:

FIG. 1 is a diagrammatic perspective view of the present invention cleaning an intracavity probe;

FIG. 2 is a diagrammnatic side elevational view taken generally in the direction of arrow 2 in FIG. 1; and FIG. 3 is a diagrammatic cross sectional view taken on line 3—3 in FIG. 2.

LIST OF REFERENCE NUMERALS UTILIZED IN THE DRAWING 10 station for soaking intracavity probes of the present invention
12 intracavity probes
13 electrical connectors of intracavity probes 12
14 housing for resting on generally horizontal surface 16
15 electrical cords of intracavity probes 12
16 generally horizontal surface
18 at least two containers
20 bottom wall of housing 14 for resting on generally horizontal surface 16
22 rear wall of housing 14 for mounting to substantially vertical surface
24 rearmost edge of bottom wall 20 of housing 14
26 pair of side walls of housing 14
28 outermost edges of bottom wall 20 of housing 14
30 front cross member of housing 14
32 forwardmost edges 32 of pair of side walls 26 of housing 14
34 top cross member of housing 14
36 uppermost edge of pair of side walls 26 of housing 14
40 first partition 40 in housing 14
42 rearwardmost edge of top cross member 34 of housing 14
44 plurality of louvers through first partition 40 of housing 14
46 noxious and/or toxic fumes emanating from disinfectant in at least one container of at least two containers 18 in which intracavity probes 12 are soaked
48 second partition in housing 14
50 third partition in housing 14
52 fourth partition in housing 14
54 forwardmost edge of top cross member 36 of housing 14
58 container compartment in housing 14
60 open top of container compartment 58 in housing 14
62 open front of container compartment 58 in the housing 14
64 filter compartment in housing 14
66 carbon filter for filtering out noxious and/toxic fumes 46 passing therethrough
68 electrical connector compartment in housing 14
69 open top of electrical connector compartment 69 in housing 14 for holding electrical connectors 13 of intracavity probes 12 while intracavity probes 12 are being soaked in at least two containers 18
70 notches in forwardmost edge 54 of top cross member 36 of housing 14
72 adjustable holder clips for clipping onto electrical cords 15
74 machine compartment in housing 14
76 electric fan contained in machine compartment 74 in housing 14
78 plurality of vent holes in at least one side wall of pair of side walls 26 of housing 14
80 power cable passing through one side wall of pair of side walls 26 of housing 14
82 on/off switch 82 in one side wall of pair of side walls 26 of housing 14
84 open top of each container of at least two containers 18 for preventing cross contamination when inserting and removing intracavity probes 12
86 screw top lid that seals open top 84 of each container of at least two containers 18 for preventing cross contamination when inserting and removing intracavity probes 12

DETAILED DESCRIPTION OF THE PREFERRED EMBODIMENT

Referring now to the figures, in which like numerals indicate like parts, and particularly to FIGS. 1–3, the station for soaking intracavity probes of the present invention is shown generally at 10 for soaking intracavity probes 12 that have electrical connectors 13 and electrical cords 15 that connect the intracavity probes 12 to their associated electrical connector of the electrical connectors 13.

The station for soaking intracavity probes 10 comprises a housing 14 for resting on a generally horizontal surface 16.

The station for soaking intracavity probes 10 further comprises at least two containers 18, with at least one container of the at least two containers being for containing a disinfectant in which the intracavity probes 12 are soaked, and with another container of the at least two containers 18 being for containing a rinse agent in which the intracavity probes 12 are rinsed after they have been soaked.

The at least two containers 18 are replaceably positioned in the housing 14.

The housing 14 comprises a bottom wall 20 for resting on the generally horizontal surface 16.

The housing 14 further comprises a rear wall 22 for mounting to a substantially vertical surface, and which extends perpendicularly upwardly from the bottom wall 20 of the housing 14, at its rearmost edge 24.

The housing 14 further comprises a pair of side walls 26 that extend perpendicularly upwardly from the bottom wall 20 of the housing 14, at its outermost edges 28.

The housing 14 further comprises a front cross member 30 that is elongated and slender and extends transversely from one side wall of the pair of side walls 26 of the housing 14 to another side wall of the pair of side walls 26 of the housing 14, at their forwardmost edges 32, and is spaced upward of the bottom wall 20 of the housing 14.

The housing 14 further comprises a top cross member 34 that is elongated and slender and extends transversely from the one side wall of the pair of side walls 26 of the housing 14 to the another side wall of the pair of side walls 26 of the housing 14, at their uppermost edges 36.

The housing 14 further comprises a first partition 40 that is spaced parallelally behind the front cross member 34 of the housing 14 and extends perpendicularly upwardly from the bottom wall 20 of the housing 14 to the top cross member 34 of the housing 14, at its rearwardmost edge 42.

The first partition 40 of the housing 14 has a plurality of louvers 44 therethrough that are slender, elongated, horizontally-oriented, and vertically spaced-apart, and which extend from substantially an elevation of the front cross member 34 of the housing 14 to substantially the top cross member 36 of the housing 14, and for allowing noxious and/or toxic fumes 46 emanating from the disinfectant in the at least one container of the at least two containers 18 in which the intracavity probes 12 are soaked, to pass therethrough.

The housing 14 further comprises a second partition 48 that is spaced parallelally behind the first partition 40 of the housing 14 and extends perpendicularly upwardly from the bottom wall 20 of the housing 14 to the top cross member 34 of the housing 14, at its rearwardmost edge 42.

The second partition 48 of the housing 14 is a screen-like material for allowing the noxious and/or toxic fumes 46 to pass therethrough.

The housing 14 further comprises a third partition 50 that is spaced parallelally behind the second partition 48 of the housing 14 and extends perpendicularly upwardly from the bottom wall 20 of the housing 14 to an elevation below the top cross member 34 of the housing 14.

The third partition 50 of the housing 14 is a screen-like material for allowing the noxious and/or toxic fumes 46 to pass therethrough.

The housing 14 further comprises a fourth partition 52 that extends perpendicularly rearwardly from the second partition 48 of the housing 14 to the rear wall 22 of the housing 14, at an elevation below the top cross member 36 of the housing 14.

The pair of side walls 26 of the housing 14 slant rearwardly from the front cross member 30 of the housing 14 to the top cross member 36 of the housing 14, at its forwardmost edge 54.

The bottom wall 20 of the housing 14, the pair of side walls 26 of the housing 14, the front cross member 30 of the housing 14, the top cross member 36 of the housing, and the first partition 40 of the housing 14 define a container compartment 58 that is open and replaceably holds the at least two containers 18, with the slant of the pair of side walls 26 of the housing 14 allowing the at least two containers 18 to be inserted and removed from the container compartment 58 in the housing 14, from its open top 60, and with the front cross member 30 of the housing 14 preventing the at least two containers 18 from falling out of the container compartment 58 in the housing 14, from its open front 62.

The bottom wall 20 of the housing 14, the pair of side walls 26 of the housing 14, the second partition 48 of the housing 14, the third partition 50 of the housing 14, and the fourth partition 52 of the housing 14 define a filter compartment 64 in which a carbon filter 66 resides for filtering out the noxious and/toxic fumes 46 passing therethrough.

The pair of side walls 26 of the housing 14, the rear wall 22 of the housing 14, the second partition 48 of the housing 14, and the fourth partition 52 of the housing 14 define an electrical connector compartment 68 that has an open top 69 for holding the electrical connectors 13 of the intracavity probes 12 while the intracavity probes 12 are being soaked in the at least two containers 18 which keeps the electrical connectors 13 of the intracavity probes 12 safely out of the way during soaking, with the electrical cords 15 being draped over the top cross member 36 of the housing 14 and passing through notches 70 in the forwardmost edge 54 of the top cross member 36, and with the intracavity probes 12 being suspended in the at least two containers 18 for preventing costly damage to sensitive tips of the intracavity probes 12 by adjustable holder clips 72 for clipping onto the electrical cords 15, and which rest on the top cross member 36 of the housing 14.

The bottom wall 20 of the housing 14, the pair of side walls 26 of the housing 14, the rear wall 22 of the housing 14, the third partition 50 of the housing 14, and the fourth partition 52 of the housing 14 define a machine compartment 74.

The machine compartment 74 in the housing 14 contains an electric fan 76 that is disposed in proximity of the bottom wall 20 of the housing 14 and the rear wall 22 of the housing 14, and being for moving the noxious and/or toxic fumes 46 from the container compartment 62 in the housing 14 through the plurality of louvers 44 in the first partition 40 in the housing 14, through the second partition 48 in the housing 14, through the carbon filter 64, through the third partition 50 in the housing 14, and out through a plurality of vent holes 78 in at least one side wall of the pair of side walls 26 of the housing 14.

One side wall of the pair of side walls 26 of the housing 14 has a power cable 80 that passes therethrough to electrical communication with, and powers, the electric fan 76.

The one side wall of the pair of side walls 26 of the housing 14 further has an on/off switch 82 that is in electrical communication with the power cable 80 and selectively activates the electric fan 76.

Each container of the at least two containers 18 has an open top 84 that is 3.5" wide for preventing cross contamination when inserting and removing the intracavity probes 12, and which can be sealed by a screw top lid 86 when not in use to prevent evaporation.

It will be understood that each of the elements described above, or two or more together, may also find a useful application in other types of constructions differing from the types described above.

While the invention has been illustrated and described as embodied in a soaking station for intracavity probes, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A station for soaking intracavity probes, wherein the intracavity probes have electrical connectors and electrical cords that connect the intracavity probes to their associated electrical connector of the electrical connectors, said station comprising:

a) a housing for either resting on a generally horizontal surface or mounting to a generally vertical surface; and
   b) at least two containers replaceably positioned in said housing, with at least one container of said at least two containers being for containing a disinfectant in which the intracavity probes are soaked, and with another container of said at least two containers being for containing a rinse agent in which the intracavity probes are rinsed after they have been soaked;

wherein said housing comprises:
   i) a bottom wall for resting on the generally horizontal surface;
   ii) a pair of side walls extending perpendicularly upwardly from said bottom wall of said housing, at its outermost edges;

iii) a front cross member extending transversely from one side wall of said pair of side walls of said housing to another side wall of said pair of side walls of said housing, at their forwardmost edges, and being spaced upward of said bottom wall of said housing;

iv) a top cross member extending transversely from said one side wall of said pair of side walls of said housing to said another side wall of said pair of side walls of said housing, at their uppermost edges; and v) a first partition being spaced parallelally behind said front cross member of said housing and extending perpendicularly upwardly from said bottom wall of said housing to said top cross member of said housing, at its rearwardmost edge; said first partition in said housing having a plurality of louvers therethrough being horizontally-oriented, vertically spaced-apart, and extending from substantially an elevation of said front cross member of said housing to substantially said top cross member of said housing, and being for allowing noxious and/or toxic fumes emanating from the disinfectant in said at least one container of said at least two containers in which the intracavity probes are soaked to pass therethrough.

2. The station as defined in claim 1, wherein said housing further comprises a rear wall for mounting to the generally vertical surface, and which extends perpendicularly upwardly from said bottom wall of said housing, at its rearmost edge.

3. The station as defined in claim 1, wherein said housing further comprises a second partition that is spaced parallelally behind said first partition in said housing and extends perpendicularly upwardly from said bottom wall of said housing to said top cross member of said housing, at its rearwardmost edge.

4. The station as defined in claim 3, wherein said second partition in said housing is a screen material for allowing the noxious and/or toxic fumes to pass therethrough.

5. The station as defined in claim 3, wherein said housing further comprises a third partition that is spaced parallelally behind said second partition in said housing and extends perpendicularly upwardly from said bottom wall of said housing to an elevation below said top cross member of said housing.

6. The station as defined in claim 5, wherein said third partition in said housing is a screen material for allowing the noxious and/or toxic fumes to pass therethrough.

7. The station as defined in claim 5, wherein said housing further comprises a fourth partition that extends perpendicularly rearwardly from said second partition in said housing to said rear wall of said housing, at an elevation below said top cross member of said housing.

8. The station as defined in claim 7, wherein said bottom wall of said housing, said pair of side walls of said housing, said second partition in said housing, said third partition in said housing, and said fourth partition in said housing define a filter compartment in which a carbon filter resides for filtering out the noxious and/toxic fumes passing therethrough.

9. The station as defined in claim 7, wherein said pair of side walls of said housing, said rear wall of said housing, said second partition in said housing, and said fourth partition in said housing define an electrical connector compartment that has an open top for holding the electrical connectors of the intracavity probes while the intracavity probes are being soaked in said at least two containers which keeps the electrical connectors of the intracavity probes safely out of the way during soaking, with the electrical cords being draped over said top cross member of said housing and passing through notches in said forwardmost edge of said top cross member, and with the intracavity probes being suspended in said at least two containers for preventing costly damage to sensitive tips of the intracavity probes, by adjustable holder clips for clipping onto the electrical cords, and which rest on said top cross member of said housing.

10. The station as defined in claim 7, wherein said bottom wall of said housing, said pair of side walls of said housing, said rear wall of said housing, said third partition in said housing, and said fourth partition in said housing define a machine compartment.

11. The station as defined in claim 10, wherein said machine compartment in said housing contains an electric fan that is disposed in proximity of said bottom wall of said housing and said rear wall of said housing 14, and is for moving the noxious and/or toxic fumes from said container compartment in said housing through said plurality of louvers in said first partition in said housing, through said second partition in said housing, through said carbon filter, through said third partition in said housing, and out through a plurality of vent holes in at least one side wall of said pair of side walls of said housing.

12. The station as defined in claim 11, wherein one side wall of said pair of side walls of said housing has a power cable that passes therethrough to electrical communication with, and powers, said electric fan.

13. The station as defined in claim 12, wherein said one side wall of said pair of side walls of said housing further has an on/off switch that is in electrical communication with said power cable and selectively activates said electric fan.

14. The station as defined in claim 1, wherein said pair of side walls of said housing slant rearwardly from said front cross member of said housing to said top cross member of said housing, at its forwardmost edge.

15. The station as defined in claim 14, wherein said bottom wall of said housing, said pair of side walls of said housing, said front cross member of said housing, said top cross member of said housing, and said first partition in said housing define a container compartment that is open and replaceably holds said at least two containers, with said slant of said pair of side walls of said housing allowing said at least two containers to be inserted and removed from said container compartment in said housing, from its open top, and with said front cross member of said housing preventing said at least two containers from falling out of said container compartment in said housing, from its open front.

16. The station as defined in claim 1, wherein each container of said at least two containers has an open top that is 3.5" wide for preventing cross contamination when inserting and removing the intracavity probes, and which can be sealed by a screw top lid when not in use to prevent evaporation.

* * * * *